US005202048A

United States Patent [19]

Bartolo et al.

[11] Patent Number: 5,202,048

[45] Date of Patent: Apr. 13, 1993

[54] PERSONAL CLEANSING PRODUCT WITH ODOR COMPATIBLE BULKY AMINE CATIONIC POLYMER WITH REDUCED ODOR CHARACTERISTICS

[75] Inventors: Robert G. Bartolo, Cincinnati; Louis F. Wong, Mason, both of Ohio

[73] Assignee: The Procter & Gamble Company, Cincinnati, Ohio

[21] Appl. No.: 816,523

[22] Filed: Dec. 30, 1991

Related U.S. Application Data

[63] Continuation of Ser. No. 374,315, Jun. 30, 1989, abandoned.

[51] Int. Cl.[5] ........................ A61K 7/50; C11D 3/37; C11D 3/46; C11D 13/18

[52] U.S. Cl. .................................. 252/117; 252/121; 252/132; 252/134; 252/174; 252/174.15; 252/174.17; 252/174.23; 252/544; 252/547; 252/DIG. 2; 252/DIG. 5; 252/DIG. 14; 252/DIG. 16; 424/70; 424/78.03

[58] Field of Search ............... 252/117, 132, 547, 544, 252/174.23, 174.15, 174.17, DIG. 2, DIG. 5, DIG. 14; 424/70, 78

[56] References Cited

U.S. PATENT DOCUMENTS

| | | | |
|---|---|---|---|
| 2,876,217 | 3/1959 | Paschall | 260/233.3 |
| 3,589,978 | 6/1971 | Kamal et al. | 162/158 |
| 4,061,602 | 12/1977 | Oberstar et al. | 252/547 |
| 4,298,494 | 11/1981 | Parslow et al. | 252/174.16 |
| 4,454,060 | 6/1984 | Lai et al. | 252/547 |
| 4,477,375 | 10/1984 | Grollier | 252/542 |
| 4,540,507 | 9/1985 | Grollier | 252/174.23 |
| 4,663,159 | 5/1987 | Brode, II et al. | 424/70 |
| 4,678,606 | 7/1987 | Akhter et al. | 252/542 |
| 4,704,224 | 11/1987 | Saud | 252/132 |
| 4,710,314 | 12/1987 | Madrange et al. | 252/117 |
| 4,714,563 | 12/1987 | Kajs et al. | 252/107 |
| 4,758,282 | 7/1988 | Stober et al. | 127/34 |
| 4,764,365 | 8/1988 | Boothe et al. | 424/81 |
| 4,820,447 | 4/1989 | Medcalf et al. | 252/117 |
| 4,832,872 | 5/1989 | Scandel | 252/547 |
| 4,874,538 | 10/1989 | Dawson et al. | 252/117 |

FOREIGN PATENT DOCUMENTS 1136842 12/1968 United Kingdom .

*Primary Examiner*—Dennis Albrecht
*Attorney, Agent, or Firm*—Betty J. Zea; Leonard Williamson; Robert B. Aylor

[57] ABSTRACT

Personal cleansing compositions containing surfactant and selected cationic polymer provide products having improved odor stability. This "bulky amine" cationic polymer is: Guar (POLYMER)-$CR^1HCR^2R^3$—$CH_2NR^4R^5R^6$ wherein $R^1$-$R^3$ is a —H or —OH substituent, and wherein at least one of $R^4$, $R^5$ and $R^6$ are selected from the group consisting of alkyl having a chain length of from about 2 to about 24 carbon atoms, and alkoxy alkyl containing from about 2 to about 12 carbon atoms, and mixtures thereof. The cationic polymer is less odoriferous than trimethylamine-based cationic polymers. The personal cleansing composition ash a pH of at least 7.5 in a 1% aqueous solution.

8 Claims, No Drawings

PERSONAL CLEANSING PRODUCT WITH ODOR COMPATIBLE BULKY AMINE CATIONIC POLYMER WITH REDUCED ODOR CHARACTERISTICS

This is a continuation of application Ser. No. 07/374,315, filed on Jun. 30, 1989, now abandoned.

FIELD OF THE INVENTION

This invention pertains to personal cleansing compositions for personal washing, which compositions comprise quaternary amine polymers.

BACKGROUND OF THE INVENTION

Liquid and solid bar compositions based on soap and/or synthetic surfactants are commonly used for cleansing the human body. A wide variety of additives have been suggested for inclusion in said compositions. Some enhance the physical properties, e.g., bar hardness, wear rate, resistance to water. Others enhance the in-use properties such as lather characteristics and some impact on the impression the composition has on the skin both during washing (bar feel) and afterwards.

It has been discovered that the addition of certain polymeric materials to such liquids and bars can have a beneficial skin mildness effect for the user without deleteriously affecting other product properties. In general, the useful polymers should be soluble or dispersible in water to a level of at least 1% by weight, preferably at least 5% by weight at 25° C. Suitable polymers are high molecular weight materials (mass-average molecular weight determined, for instance, by light scattering, being generally from about 20,000 to about 5,000,000, preferably from about 50,000 to about 4,000,000, and more preferably from about 500,000 to about 3,000,000) and preferably have a thickening ability such that a 1% dispersion of the polymer in water at 20° C. exceeds about 1 PaS(1O poise) at a shear rate of $10^{-2}$ $sec^{-1}$ Useful polymers are the cationic, nonionic, amphoteric, and anionic polymers useful in the cosmetic field. Preferred are cationic and nonionic resins and mixtures thereof. Highly preferred are the cationic resins.

To date the preferred cationic polymers include cationic guar gums such as hydroxyproxyltrimethylammonium guar gum.

However, it has been discovered that there is an odor problem with using such "cationic trimethylamine quaternized polymers" in compositions having a pH of 7.5 or above. They break down and release odoriferous labile amines.

Odoriferous labile amines are detectable at levels as low as 2 ppb. Personal cleansing products containing odoriferous quaternary amine polymers are disclosed in one or more of the following patents:

| Pat. No. | Date | Inventor(s) |
|---|---|---|
| US 3,761,418 | 9/1973 | Parran, Jr.; |
| US 4,234,464 | 11/1980 | Morshauser; |
| US 4,061,602 | 12/1977 | Oberstar et al.; |
| US 4,472,297 | 9/1984 | Bolich et al.; |
| US 4,491,539 | 1/1985 | Hoskins et al.; |
| US 4,540,507 | 9/1985 | Grollier; |
| US 4,673,525 | 6/1987 | Small et al.; |
| US 4,704,224 | 11/1987 | Saud; and |
| Jap. J57105 | 6/30/82 | Pola. |

All of the above patents are hereby incorporated herein by reference, especially their for basic personal cleansing product and quat polymer disclosures.

SUMMARY OF THE INVENTION

The present invention relates to a personal cleansing product made with a selected quaternized cationic polymer wherein each quaternary ammonium moiety is derived from a bulky amine. The preferred product is a toilet bar.

OBJECTS OF THE INVENTION

An object of the present invention is to provide an improved toilet bar, preferably a soap bar, comprising a cationic polymeric skin conditioning agent which does not comprise a potential odoriferous amine moiety.

Other objects will become apparent from the detailed description below.

DETAILED DESCRIPTION OF THE INVENTION

The present invention comprises basic personal cleansing compositions comprising from about 0.2% to about 5% by weight selected cationic polymer wherein each cationic group is derived from a "bulky" amine. Compared to personal cleansing compositions which are prepared with cationic polymers which comprise a potential labile amine moiety, e.g., trimethylamine-based cationic polymers, the compositions of this invention consistently exhibit superior odor stability due to the selected "bulky amine" cationic polymers. The term "basic personal cleansing compositions" as used herein means that the composition has a pH of at least about 7.5, preferably at least about 8.5.

While not being bound to any theory, illustrations A and B show the theoretical degradation of labile amine containing cationic polymers in a basic environment. Generic degradation:

$$\text{Polymer-CHR—CH}_2\text{—N}^+(\text{CH}_3)_3. \rightarrow \text{polymer—CR=CH}_2 + \text{N(CH}_3)_3 \quad \text{(A)}$$

where R can be meant to represent any group (e.g., H, OH, alkyl chain); e.g., $$\text{Guar-CH}_2\text{—O—CH}_2\text{—C—H(OH)—CH-}_2\text{—N}^+(\text{CH}_3)_3 \rightarrow \text{Guar-CH}_2\text{—O—CH}_2\ \text{C(OH)=CH}_2 + \text{N(CH}_3)_3 \quad \text{(B)}$$

The extent of this degradation and the effect of it on product odor were not appreciated heretofore. The level of hydration required to cause a problem is very low and therefore it is extremely difficult to detect and identify the offending material.

The Bulky Amine Cationic Polymers

Bulky amine polymers are defined herein as POLYMERS with the following non-labile cationic functional group:

(I) $\text{(POLYMER)—CR}^1\text{H—CR}^2\text{R}^3\text{—NR}^4\text{R}^5\text{R}^6$ wherein $R^1$–$R^3$ is H or any other substituent and $R^4$, $R^5$ and $R^6$ combine with N to form a pendant amine which when free has less odor impact than trimethylamine, preferably at least one of $R^4$, $R^5$ and $R^6$ is alkyl having a chain length of from about 2 to about 24 carbon atoms, or an alkoxy alkyl group containing from about 2 to about 12 carbon atoms.

Some examples of preferred bulky amine polymers are cationic guar gums having the following structures;

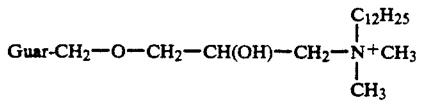

(II)

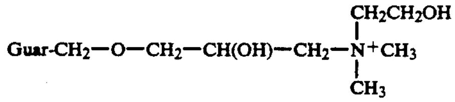

(III)

An example of a bulky amine hydroxyethyl cellulose (HEC) polymer is:

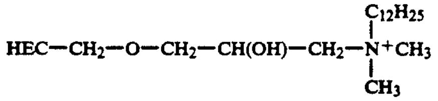

(IV)

These "bulky amine" groups add additional complexity to the preparation of the polymer and the finished compositions. They would not be used, except for the existence of the odor problem with the trimethylamine derived polymer. They may also have improved skin conditioning benefits.

The composition of this invention preferably comprises from about 0.2% to about 5%, preferably from about 0.5% to about 2%, of the cationic polymer. The average molecular weight of the preferred cationic guar gum is from about 50,000 to about 1,000,000, preferably from about 100,000 to about 500,000, and more preferably from about 250,000 to about 400,000 and the degree of substitution is from about 0.5 to about 4, preferably from about 1 to about 2.5. Some preferred cationic guars (galactomannans) are disclosed in U.S. Pat. No. 4,758,282, Stober et al., issued Jul. 19, 1988, incorporated herein by reference. The cationic guar gum polymers disclosed in commonly assigned U.S. patent application Ser. No. 07/266,039, J. R. Knochel and P. E. Vest, filed Nov. 2, 1988, would be suitable when the cationic groups are substituted with bulky amine groups.

Other bulky amine cationic polymeric skin conditioning agents useful in the present invention have molecular weights of from 1,000 to 3,000,000. Useful polymers are selected from the group consisting of:

(I) cationic polysaccharides;

(II) cationic copolymers of saccharides and synthetic cationic monomers, and (III) synthetic polymers selected from the group consisting of any other synthetic polymer containing pendant quaternary amine groups, e.g., quaternized silicones and quaternized methacrylates.

Specific examples of members of the bulky amine cationic polysaccharide class include the cationic hdyroxyethyl cellulose, e.g., LM-200 made by Union Carbide Corporation.

The cationic copolymers of saccharides and synthetic cationic monomers useful in the present invention encompass those containing the following saccharides: glucose, galactose, mannose, arabinose, xylose, fucose, fructose, glucosamine, galactosamine, glucuronic acid, galacturonic acid, and 5 or 6 membered ring polyalcohols. Also included are hydroxymethyl, hydroxyethyl and hydroxypropyl derivatives of the above sugars.

The boiling points of some exemplary substituted amines are set out in Table 1.

TABLE 1

| Eliminated Amine | Boiling Point/°C. |
| --- | --- |
| Labile Amine | |
| Trimethylamine | 3 |
| Bulky Amine | |
| Dimethylethylamine | 36 |
| Methyldiethylamine | 63 |
| Triethylamine | 89 |
| Dimethyloctylamine | 195 |
| Dimethylcyclohexylamine | 158 |
| Dimethylbenzylamine | 183 |
| Dimethylethanolamine | 133 |
| Diethylethanolamne | 161 |

For a homologous series of compounds (e.g., tri-substituted amines), volatility decreases with increasing molecular weight. Volatility is dependent, among other things on the boiling point of the neat component. Odor impact also has a strong dependence on the amount of volatilized material that reaches the nose. Table 1 demonstrates the significant effect which adding "bulky" groups has on volatility and, hence, odor impact of amines. For pure hydrocarbon substitution, the larger the alkyl chains (or the larger than degree of long chain substitution) the lower the odor impact. Thus, bulky amines have boiling points of greater than ambient temperature, and preferably at least about 30° C., more preferably more than about 80° C.

The Surfactant Component

The surfactant component of the present compositions comprises alkali metal soap or synthetic surfactant or mixtures thereof.

Alkali metal soaps can be made by direct saponification of the fats and oils or by the neutralization of the free fatty acids which are prepared in a separate manufacturing process. Particularly useful are the sodium and potassium salts of the mixtures of fatty acids derived from coconut oil and tallow, i.e., sodium and potassium tallow and coconut soaps.

The term "tallow" is used herein in connection with fatty acid mixtures which typically have an approximate carbon chain length distribution of 2.5% $C_{14}$, 29% $C_{16}$, 23% $C_{18}$, 2% palmitoleic, 41.5% oleic and 3% linoleic. (The first three fatty acids listed are saturated.) Other mixtures with similar distribution, such as the fatty acids derived from various animal tallows. The tallow can also be hardened (i.e., hydrogenated) to convert part or all of the unsaturated fatty acid moieties to saturated fatty acid moieties.

When the terms "coconut oil" and "coconut fatty acid" (CNFA) are used herein, they refer to fatty acid mixtures which typically have an approximate carbon chain length distribution of about 8% $C_7$, 7% $C_{10}$, 48% $C_{12}$, 17% $C_{14}$, 9% $C_{16}$, 2% $C_{18}$, 7% oleic, and 2% linoleic. (The first six fatty acids listed are saturated.) Other sources having similar carbon chain length distribution such as palm kernel oil and babassu kernel oil are included with the terms coconut oil and coconut fatty acid.

A preferred soap bar of this invention comprises soap as its primary or sole surfactant It also contains as an essential ingredient a skin conditioning amount of a hydrated, cationic guar gum provided by a cationic guar gum polymer. This polymer is uniformly distributed in the soap bar matrix without affecting the smooth feel of the dry or wet bar.

Another preferred toilet bar is based on mild synthetic surfactants as disclosed in commonly assigned U.S. Pat. No. 4,673,525, Small et al., issued Jun. 16, 1987, incorporated herein by reference.

Synthetic detergents can also be present in compositions herein. Preferred types of synthetic detergents are of the anionic or nonionic type. Examples of anionic synthetic detergents are the salts of organic sulfuric reaction products such as alkyl sulfates having the formula $R_{24}OSO_3M$;

alkyl sulfonates having the formula $R_{24}SO_3M$;

alkyl ether sulfates having the formula $R_{24}(OC_2H_4)_x$-$OSO_3M$;

alkyl mono glyceride sulfonates having the formula

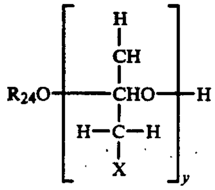

and alkyl benzene sulfonates having the formula

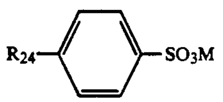

In the above formulae, $R_{24}$ is a straight or branched chain alkyl of from about 8 to about 24 carbon atoms; M is an alkali metal or ammonium ion; x is a number of from 1 to about 10; y is a number of from 1 to 4; and X is selected from the group consisting of chlorine, hydroxyl, and $-SO_3M$, at least one X in each molecule being $-SO_3M$. Examples of nonionic synthetic detergents are ethoxylated fatty alcohols (e.g., the reaction product of one mole of coconut fatty alcohol with from about 3 to about 30 moles of ethylene oxide) and fatty acid amides such as coconut fatty acid monoethanolamide and stearic acid diethanolamide. Although it may be desirable in some instances to incorporate synthetic detergents into the compositions of the present invention, the compositions herein can be free of synthetic detergents. Preferred are the mild synthetic surfactants disclosed in U.S. Pat. No. 4,673,525, Small et al., issued Jun. 16, 1987, incorporated herein by reference.

Insoluble Alkaline Earth Metal Soaps

Insoluble alkaline earth metal soaps such as calcium stearate and magnesium stearate can also be incorporated into compositions of the present invention at levels up to about 30%. These materials are particularly useful in toilet bars in which synthetic detergents are present in that they tend to reduce the relatively high solubility which such bars normally have. These alkaline earth metal soaps are not included within the term "soap" as otherwise used in this specification. The term "soap" as used herein refers to the alkali metal soaps.

Optional Components

The compositions of the present invention can contain optional components such as those conventionally found in personal cleansing products. Conventional antibacterial agents can be included in the present compositions at levels of from about 0.5% to about 4%. Typical antibacterial agents which are suitable for use herein are 3,4-di and 3,4',5-tribromosalicyla-anildes; 4,4'-dichloro-3-(trifluoromethyl)carbanilide; 3,4,4'-trichlorocarbanilide and mixtures of these materials. Conventional nonionic emollients can be included as additional skin conditioning agents in the compositions of the present invention at levels up to about 40%, preferably at levels of from about 1% to about 25%. Such materials include, for example, mineral oils, paraffin wax having a melting point of from about 100° F., fatty sorbitan esters (see U.S. Pat. No. 3,988,255, Seiden, issued Oct. 26, 1976, incorporated by reference herein), lanolin and lanolin derivatives, esters such as isopropyl myristate and triglycerides such as coconut oil or hydrogenated tallow.

Free fatty acid such as coconut fatty acid can be added to the compositions herein to improve the volume and quality (creaminess) of the lather produced by the compositions herein.

Conventional perfumes, dyes and pigments can also be incorporated into compositions of the invention at levels up to about 5%. Perfumes are preferably used at levels of from about 0.5% to 3% and dyes and pigments are preferably used at levels of from about 0.001% to about 0.5%.

Bar Preparation

Toilet bars of the present invention can be prepared in any conventional manner. E.g., the bulky amine cationic polymer can be added to noodles of the base soap mixture containing from about 10% to about 22% moisture in an amalgamator. Any optional ingredients such as perfumes, dyes, etc., are also added to the amalgamator. The mixture is processed in the amalgamator and milled in the conventional manner under conventional conditions. It is then extruded (plodded) into logs for cutting and stamping into toilet bars.

In a method of making the bar of the present invention, the bulky amine cationic polymer is added to soap noodle and mixed in the soap mixing steps of the soap bar making process.

The soap bars of this invention preferably contain up to 20% of a synthetic surfactant. If a synthetic surfactant is included, a mild one is preferred. A mild synthetic surfactant is defined herein as one which does relatively little damage to the barrier function of the stratum corneum. The mild surfactant is preferably used at a level of 0–20%, preferably about 2–15%. The fatty acid soap and mild surfactant mixture preferably has a ratio of 2.5:1 to 37:1, preferably from 2.5:1 to 14:1, and most preferably from 6.5:1 to 14:1, soap:synthetic.

A preferred soap bar of this invention also contains from about 2% to about 17% moisturizer, preferably one selected from glycerin and free fatty acid or mixtures thereof. The more preferred bar of this invention contains at least 4% moisturizer.

Some preferred mild synthetic surfactants useful in this invention include alkyl glyceryl ether sulfonate (AGS), anionic acyl sarcosinates, methyl acyl taurates, N-acyl glutamates, alkyl glucosides, acyl isethionates, alkyl sulfosuccinate, alkyl phosphate esters, ethoxylated alkyl phosphate esters, alkyl ether sulfates, methyl glucose esters, protein condensates, mixtures of alkyl ether sulfates and alkyl amine oxides, betaines, sultaines, and mixtures thereof. Included in the surfactants are the alkyl ether sulfates with 1 to 12 ethoxy groups, especially ammonium and sodium lauryl ether sulfates. Alkyl chain lengths for these surfactants are $C_8$–$C_{22}$, preferably $C_{10}$–$C_{18}$. The most preferred mild surfactant is sodium CN AGS.

The following examples are presented by way of illustration only.

EXAMPLES 1 AND 2

Toilet bars made using the ingredients set out in Table 2.

TABLE 2

| Ingredient | Ex. 1 Parts | Ex. 2 Parts |
|---|---|---|
| Sodium Tallowate(1) | 32.90 | 32.90 |
| Sodium Cocoate(1) | 32.90 | 32.90 |
| Water | 9.50 | 9.50 |
| Sodium Cocoglyceryl Ether Sulfonate (AGS) | 8.80 | 8.80 |
| Glycerin | 4.00 | 4.00 |
| Coconut Fatty Acid | 3.80 | 3.80 |
| Triclocarban | 1.50 | 1.50 |
| Sodium Chloride | 1.20 | 1.20 |
| Fragrance | 1.20 | 1.20 |
| Polyquaternium-7(2) | 1.00 | 1.00 |
| LM-200(3) | 1.00 | — |
| Guar-HPTC(4) | — | 1.00 |
| Titanium Dioxide | 0.35 | 0.35 |
| Tetrasodium EDTA | 0.06 | 0.06 |
| BTH(5) | 0.02 | 0.02 |
| Miscellaneous(6) | * | * |
| Totals | 100.00 | 100.00 |

(1)The values stated for sodium tallowate and sodium cocoate include a low level (>0.1%) of unsaponifiable material.
(2)The trade name for Polyquaternium-7 is Meraquat 500.
(3)LM-200 is a cationic cellulosic polymer comprising a bulky cocoyl amine.
(4)Guar HPTC is guar hydroxypropyltriammonium chloride is Jaguar C-15 (Hi-Tek). Molecular weight is about 200,000 ± 75,000.
(5)BHT is included in the respective perfume formulas to impart preservative/antioxidant properties both to the perfume and to the finished bar formula.
(6)"Miscellaneous" includes a low level of sodium sulfate and unsulfonated alcohol which come in, e.g., as a by-product of the AGS stream.

In general, making procedures common to those used for conventional toilet soap bar making are employed.

Mixing/Milling Steps

Polymer Addition Step

Plodded soap noodles are conveyed to a continuous mixer (CM) where approximately 1.0 part of cationic polymer is introduced, mixed, and plodded with the soap noodles. Uniform distribution during this addition and mixing step is important for acceptable bar feel performance. The polymer/soap noodles (generic noodles) are conveyed to milling.

Generic Milling Step

Two four-roll soap mills (feed, stationary, middle, and top rolls) are used in this step. This is a split milling (two set of mills are used in parallel) process to obtain a homogeneous mix. Efficient milling is needed in this intimate mixing step.

Dry Mixing Step

The generic noodles are conveyed to a second process system continuous mixer (CM) for the addition and mixing of other minors. This mix is plodded and conveyed to the third process CM.

Wet Mixing Step

The perfume and NaCl/sodium ethylene diamine tetra acetate (EDTA) solution are added and mixed in this wet mixing (CM) step. This finished soap formula is then plodded into soap noodles and conveyed via a transport plodder to a final milling step.

The mixture is milled using a four-roll mill, plodded, and then stamped into toilet bars of any convenient size and shape. The resulting bars are tested for odor. The bars have a pH of 9.5 in a 1% aqueous solution.

Odor Test Procedure

Polymer Cleaning

Stock samples of polymer are cleaned by swelling the polymer with water followed by extensive aeration. These "cleaned" polymers are fairly amine odor-free. After long storage times, some of these polymers exhibited a slight, but recognizable amine odor. Bulky modified polymers required little, if any, cleansing prior to testing/evaluating.

Effects Testing Procedures

The general procedure followed in evaluating the effects of pH on polymer or final product odor was to place about 200 mg of the clean polymer (or a finished product) in a screw-top vial (8 dram) and then add the test solution (buffers at pH values of 7, 10, or 14). The vials are capped and the odor allowed to build up for a short amount of time. Odor is evaluated via olfactory sensing by a panel of experts.

The pH buffers are commercially available buffers:

pH 7—$KH_2PO_4$—NaOH
pH 10—$H_3BO_3$—KOH
pH 14—1N NaOH.

TABLE 3

| Odor Evaluation of Polymers and Products Under Induced Alkaline Conditions (pH ~ 10–14) | |
|---|---|
| Polymer/Product | Odor Evaluation |
| JR-400 | Strong amine odor |
| Jaguar C-15 | Strong amine odor |
| LM-200 | No amine odor |
| Product of Ex. 1 | No amine odor |
| Product of Ex. 2 | Strong amine odor |

Note:
Ex. 1 product produced with LM-200
Ex. 2 product produced with Jaguar

JR-400 made by Union Carbide Corporation and JAGUAR C-15 made by Hi-Tek Polymers, Inc., are outside the selected polymers of this invention.

What is claimed is:

1. A personal cleansing composition comprising from about 5% to about 90% by weight of surfactant selected from the group consisting of synthetic surfactant, alkali metal soap, and mixtures thereof; and from about 0.2% to about 5% by weight bulky amine cationic polymer, said bulky amine cationic polymer being essentially free of potential labile odoriferous amine groups; wherein said bulky amine cationic polymer is: Guar (POLYMER)-$CR^1HCR^2R^3$-$CH_2NR^4R^5R^6$ wherein $R^1$–$R^3$ is a —H or —OH substituent, and wherein at least one of $R^4$, $R^5$ and $R^6$ are selected from the group consisting of alkyl having a chain length of from about 2 to about 24 carbon atoms, and alkoxy alkyl containing from about 2 to about 12 carbon atoms, and mixtures thereof; and wherein said personal cleansing composition has an alkaline pH of at least about 7.5 in a 1% aqueous solution.

2. The personal cleansing composition of claim 1 wherein aid composition is in a form selected from liquids, pastes or bars.

3. The personal cleansing composition of claim 1 wherein said cationic polymer is selected from the group consisting of:

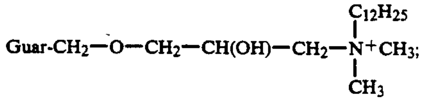

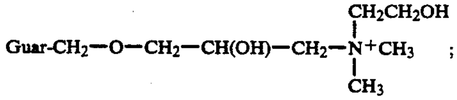

; and mixtures thereof; and
wherein said polymer has a molecular weight of from about 50,000 to about 1,000,000.

4. The personal cleansing composition of claim 1 wherein said cationic polymer is present at from about 0.5% to about 4% by weight.

5. The personal cleansing composition of claim 1 wherein said pH is at least about 8.5.

6. A process for preparing the personal cleansing composition of claim 1 comprising the steps of:

(a) forming a mixture of said cationic polymer and alkali metal soap mix noodles wherein said polymer is present in said mixture at a level to provide from about 0.2% to about 5% by weight of said polymer in said composition; said mixture containing from about 6% to about 15% moisture;

(b) milling said mixture into a uniform mixture;

(c) plodding said uniform mixture;

(d) extruding said milled and plodded mixture; and (e) stamping said extruded mixture into toilet bars.

7. The personal cleansing composition of claim 1 wherein said composition contains from about 2% to about 20% of synthetic surfactant selected from alkyl glyceryl ether sulfonates, anionic acyl sarcosinates, methyl acyl taurates, N-acyl glutamates, alkyl glucosides, acyl isethionates, alkyl sulfosuccinates, alkyl phosphate esters, ethoxylated alkyl phosphate esters, methyl glucose esters, protein condensates, mixtures of ethoxylated alkyl sulfates and alkyl amine oxides, betaines, sultaines, the alkyl ether sulfates with 1 to 12 ethoxy groups, and mixtures thereof, wherein said synthetic surfactant contains alkyl chains containing from about 8 to about 22 carbon atoms.

8. The composition of claim 7 wherein said composition contains from about 5% to about 10% of a $C_8$–$C_{18}$ alkyl glyceryl ether sulfonate.

* * * * *